United States Patent [19]

Weissman

[11] 4,332,563
[45] Jun. 1, 1982

[54] FLEXIBLE DENTAL RETAINING SPLINT
[75] Inventor: Bernard Weissman, New York, N.Y.
[73] Assignee: IPCO Corporation, White Plains, N.Y.
[21] Appl. No.: 234,857
[22] Filed: Feb. 17, 1981
[51] Int. Cl.³ .............................................. A61C 5/00
[52] U.S. Cl. ................................... 433/215; 433/225; 403/229
[58] Field of Search .................. 433/21, 225, 20, 215; 128/87 R, 87 A, 87 B, 87 C, 89 R, 92 B, 89 A, 80 C, 80 F; 403/229

[56] References Cited
U.S. PATENT DOCUMENTS
3,822,472  7/1974  Garfinkel ............................ 433/215
3,997,970 12/1976  Hodgson ............................. 433/20
4,061,939  8/1977  Hall .................................. 128/92 B Primary Examiner—Robert Peshock
Attorney, Agent, or Firm—Friedman, Goodman & Teitelbaum

[57] ABSTRACT

A flexible dental retaining splint which is disposable in a channel extending between adjacent teeth, the retaining splint being formed of a wire core with a wire coil being wound about the core with the turns of the coil being in a juxtaposition. Wire loops are formed at both ends of the wound core. The splint can also be formed with several sections of wire cores each surrounded by a wire coil and having a wire loop connecting adjacent sections. The loops function to anchor or secure the splint in the channel, either by the inlay material or pins passing through the openings provided by loops.

15 Claims, 17 Drawing Figures

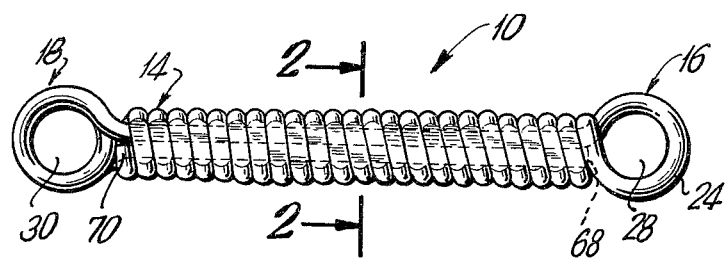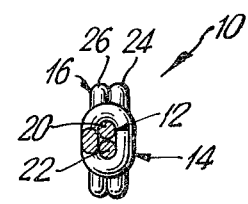
FIG.1  FIG.2
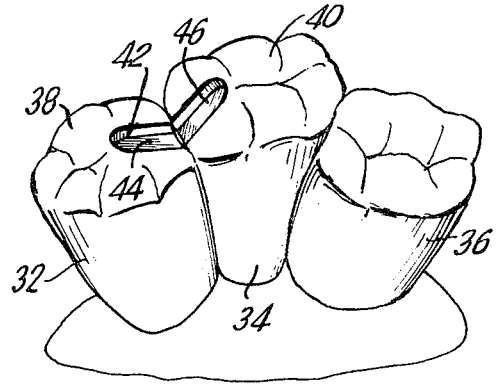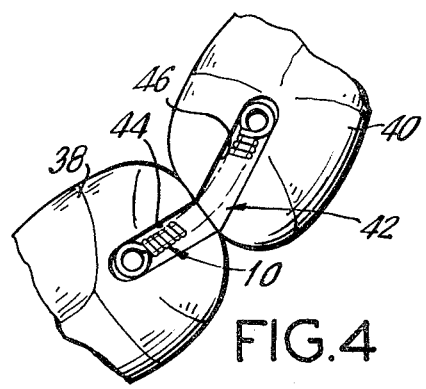
FIG.3  FIG.4
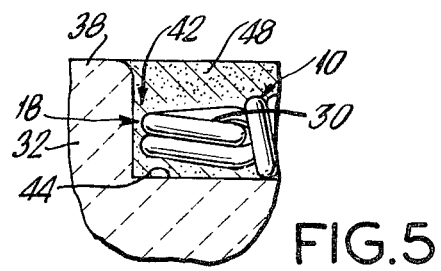
FIG.5
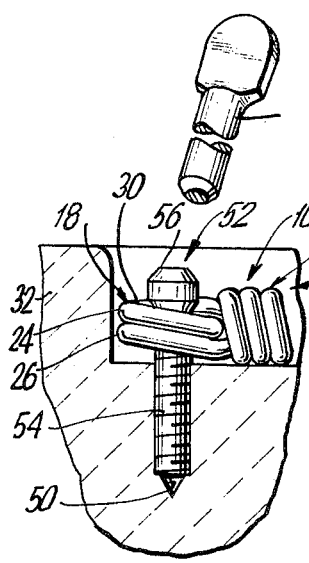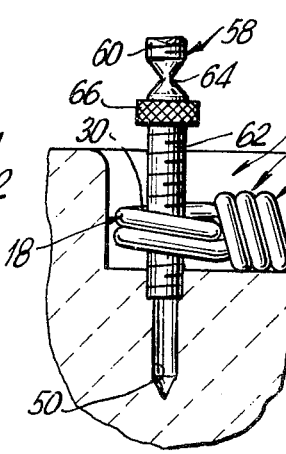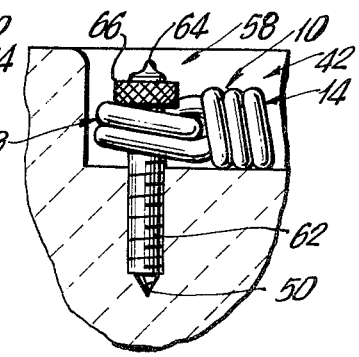
FIG.6  FIG.7  FIG.8

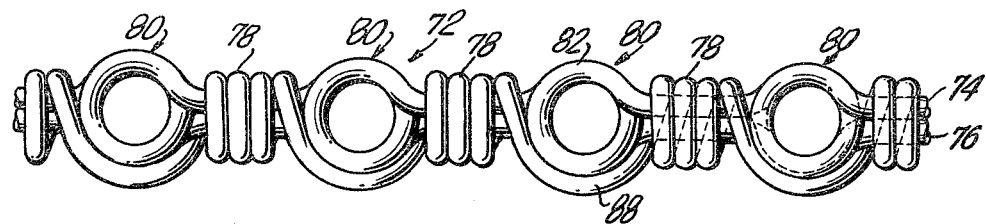
FIG.9
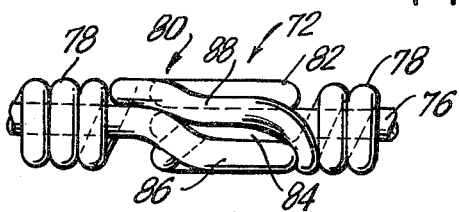
FIG.10
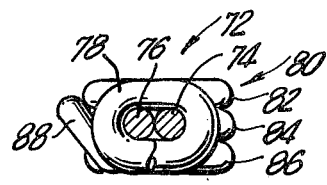
FIG.11
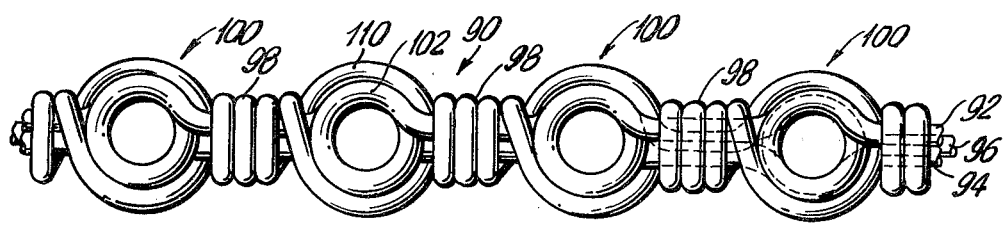
FIG.12
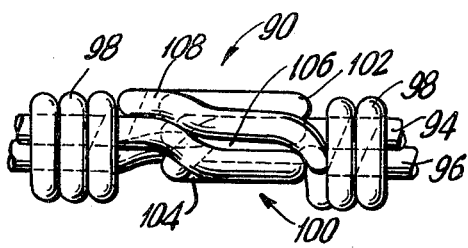
FIG.13
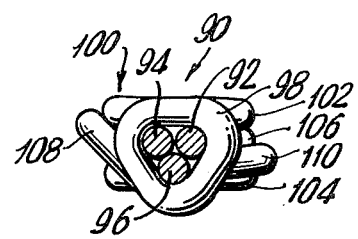
FIG.14
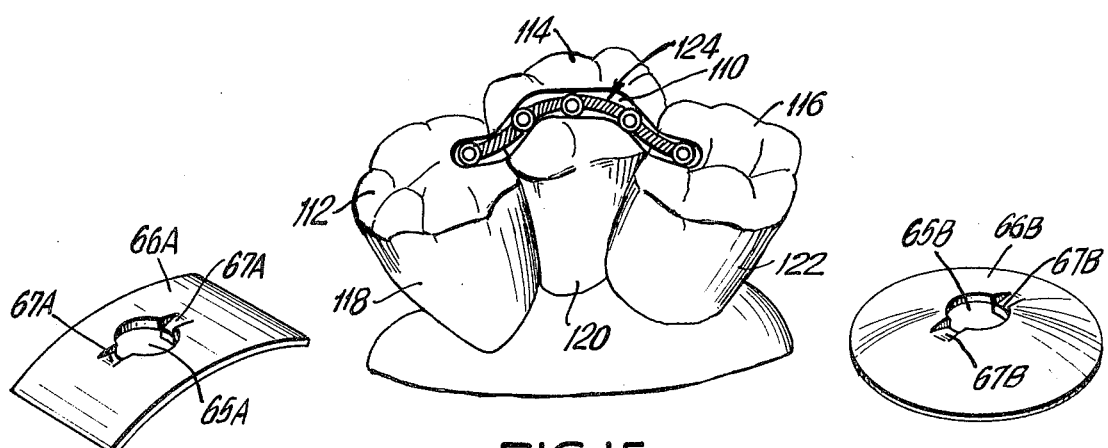
FIG.15
FIG.16
FIG.17

FLEXIBLE DENTAL RETAINING SPLINT

BACKGROUND OF THE INVENTION

This invention relates to dental splinting devices, and more particularly to a flexible dental retaining splint which can be adjusted to desired shapes for retention and reinforcement of dentition in the mouth.

The use of dental retaining splints to reinforce dentition in the mouth is one that has been well known in the dental art. However, the types of dental retaining splints have greatly limited the use of such splints and have prevented its wide application to various dental procedures. While various dental splints have been described in the prior art, most of these must be individually made by the dentist or dental technician to fit the particular shape required within the mouth structure. For example, one procedure involves forming apertures in the teeth and subsequentially forming an impression of the involved dental area. A cast model is then made from the impression including the apertures. A threaded pin is inserted through the apertures in the cast model and then a wax up of the desired splint is made. A metal splint is then cast out by the lost wax process. Finally, the splint body is disposed against the facial surfaces of the involved teeth and is secured in place by means of a screw threaded body into the splint itself.

An improvement on such procedures has been provided by various dental retaining splints which are preformed and are readily available for use by the dentist. However, such pre-formed splints are provided with standard shapes and sizes and are therefore limited to areas in the mouth that can receive such prefixed standard shapes. While some of these splints may be manipulated and bent by the dentist, the amount of flexibility is extremely limited and accordingly the shape of the splint is substantially maintained in its pre-established form.

SUMMARY OF THE INVENTION

Accordingly, it is an object of the present invention to provide a dental retaining splint which can be easily flexed by the dentist in order to accommodate a required shape within the dentition area.

Another object of the present invention is to provide a flexible dental retaining splint which can be disposed within a channel extending across adjacent teeth, and wherein the shape of the channel can be cut as is required without being limited by the shape of the retaining splint.

A further object of the present invention is to provide a flexible dental retaining splint whose length and shape can be easily modified to accommodate the need of the particular procedure.

Still another object of the present invention is to provide a flexible dental retaining splint which can be easily shaped to accommodate a required dentition, and subsequently be fixed in that shape to provide adequate reinforcement of the teeth.

Yet another object of the present invention is to provide a flexible dental retaining splint which can be cut and bent to a desired shape and which can be secured to the teeth by means of pins, screws, and the like.

Briefly, in accordance with the present invention, there is provided a flexible dental retaining splint which is disposable in a channel extending across adjacent teeth. The splint is formed of a wire core with a wire coil wound about the core. In one embodiment of the invention, wire loops are formed at both ends of the core. The loops surround apertures which face in the same direction so as to be able to receive pins which extend therethrough and continue into bores formed within the teeth. The splint can be formed of a single continuous strand of wire which forms the core, the coil, and the loops. The splint can also be formed with several sections along its length, whereby the loops interconnect adjacent sections.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is a plan view illustrating a flexible dental retaining splint in accordance with the present invention;

FIG. 2 is a cross sectional view taken along line 2—2 of FIG. 1;

FIG. 3 is a perspective view illustrating a few adjacent teeth provided with a channel to receive the flexible dental retaining splint of the present invention;

FIG. 4 is a top plan view showing the flexible dental retaining splint disposed within the channel shown in FIG. 3;

FIG. 5 is an enlarged fragmented elevational view illustrating the loop portion of the flexible dental retaining splint permanently secured in the channel of the teeth in accordance with a first method;

FIG. 6 is an elevational view similar to that shown in FIG. 5, and showing another method of securing the flexible dental splint within the channel by using a dental pin;

FIGS. 7 and 8 are elevational views similar to that shown in FIG. 6 and show various steps in securing the flexible dental retaining splint within the channel by using a different type of dental anchoring pin;

FIG. 9 is a plan view of another embodiment of the flexible dental retaining splint in accordance with the present invention;

FIG. 10 is a fragmentary side view of the embodiment shown in FIG. 9, specifically showing interconnected adjacent sections;

FIG. 11 is a sectioned end view of the embodiment shown in FIG. 9, showing a mid-section thereof;

FIG. 12 is a plan view of yet another embodiment of the flexible dental retaining splint in accordance with the present invention;

FIG. 13 is a fragmentary side view of the embodiment shown in FIG. 12, specifically showing the interconnected adjacent sections;

FIG. 14 is a sectioned end view of the embodiment shown in FIG. 12, showing a mid-section thereof;

FIG. 15 is a perspective view illustrating adjacent teeth provided with a channel and receiving the flexible dental retaining splint of FIGS. 9–14 in accordance with the present invention; and FIGS. 16 and 17 are perspective views showing different configurations of snap-on retainers for association with the dental pin of FIGS. 7 and 8.

In the various figures of the drawing, like reference characters designate like parts.

DETAILED DESCRIPTION OF THE PREFERRED EMBODIMENT

Referring now to FIGS. 1 and 2, there is shown a flexible dental retaining splint in accordance with a first embodiment of the present invention. The splint, shown generally as 10, includes a wire core, shown generally as 12 which is surrounded by a wire coil 14 and terminates at either end in wire loops 16, 18. The core is shown as being comprised of two discrete wires 20, 22, and similarly the loops each consist of two concentric turns of wire 24, 26. It will be noted that each of the loops respectively encloses a passageway 28, 30, with the passageways both facing in a same direction. The turns of the wire coil are juxtaposed to provide a rigid body member.

The dental retaining splint is formed of a suitable metal material, such as stainless steel and the like, which can be bent into different shapes in order to fit the need of a required dental procedure. Referring now to FIGS. 3-5, the use of the flexible dental retaining splint will be described. FIG. 3 shows three adjacent teeth 32, 34, and 36 such as for example adjacent bicuspids. It should be understood that the present invention is equally applicable to and between other adjacent teeth, such as the cuspids, the molars, etc. In the occlusal surfaces 38, 40 of the crowns of the teeth 32, 34, a connecting channel 42 is formed therebetween in a conventional manner. Preferably, the walls of the channel are tapered to provide a wide base at the bottom of the channel, where the tapered walls act to retain the inlay of dental material within the channel, as will be set forth below.

As shown, the channel 42 is not longitudinally straight, but has two sectional arms 44, 46 which are angularly positioned with respect to each other.

In the prior art, it would have been necessary to form an impression of the channel, form a cast model from the impression, make a wax up of the desired splint, and ultimately cast the splint body. Alternately, if a standard splint would be utilized, it would have been difficult to suitably bend the standard elongated shaped splint into the desired shape as is required to fit the angularly shaped channel 42.

As shown in FIG. 4, the flexible dental retaining splint 10 has been bent to the desired shape so as to suitably fit within the angularly shaped channel 42. The splint, although flexible in that it can be manipulated, is nevertheless stiff and strong whereby a substantial amount of force is required to bend it, so that when positioned in the channel it will retain its shape. The juxtaposition of the turns of the wire coil 14 maintain the splint in its straight or bent configuration due to the interaction between the side-by-side turns.

After the flexible dental retaining splint 10 is placed in the channel 42, an inlay 48 of dental restorative material such as precious metal, amalgam, composite resin, ceramic, porcelin, or other suitable material, is disposed in the channel 42 over the dental splint 10, as shown in FIG. 5, to cover and complete the dental procedure. The inlay 48 passes through the openings 28, 30 in the loops 16, 18 to secure or anchor the splint 10 in place. Such dental inlays are well known in the dentistry art. Thus, the flexible dental retaining splint is securely retained in place in the channel and provides the required reinforcement of the dentition.

In order to provide further rigidity to the desired shape of the flexible dental splint, it is possible to impregnate the splint with a material, or to provide the splint with a coating of material, which material is capable of being hardened at a later time. By way of example, the flexible dental retaining splint can be impregnated with solder or provided with a solder coating. The splint still retains its flexibility so that the dentist can suitably bend and shape the splint to fit the desired channel shape. Once the splint is bent to the channel shape, the dentist can then apply heat through any heated instrument, as he may commonly use in connection with other procedures. The heat applied to the flexible dental retaining splint will cause the solder therein or thereon to harden thereby fixing the shape of the splint. The splint can then be positioned in the channel, and the inlay heretofore described can then be deposited to fill the channel.

Furthermore, it may be desired to coat the splint with a plastic or silicone material, or like material, to encapsulate the splint for sanitary reasons, or to make the splint opaque to be comparable with the inlay to avoid any shadow effect, or for other reasons known in the dental art.

The flexible dental retaining splint can be further secured in the channel by pinning its ends to the teeth utilizing the passageways defined by the loops. Specifically, as is shown in FIG. 6, a bore 50 is formed in the tooth 32 through the bottom wall of the channel. The bore 50 is suitably positioned so as to axially lie beneath the passageway 30 defined by the loop 18 at one end of the flexible dental retaining splint 10. A pin can then be inserted through the passageway 30 and received within the bore 50 to secure the retaining splint in the channel.

As is shown in FIG. 6, a self-threading dental anchor 52 of the type described in U.S. Pat. No. 3,675,329 is utilized to pin the splint in place. The anchor includes a threaded shaft portion 54 which threads into the bore, and a head portion 56 which is tightened against the loop 18 before the manipulating portion 57 is broken off. It should be noted, that it is preferable not to bottom out the screw portion of the anchor, but rather to permit a slight space at the bottom of the bore which is free of the screw portion. It has been found that this will prevent cracks in the teeth, both when tightening the screw portion as well as subsequently when the screw portion is retained in place within the teeth.

A similar bore and dental anchor can be placed at the opposite end of the dental retaining splint so as to pin both ends in place. Subsequently, inlay material can be placed into the channel to retain the splint in place and finish the procedure.

Instead of utilizing the above dental anchor 52, a standard screw or a dental anchoring pin of the type described in U.S. Pat. No. 3,675,328 can be utilized. Specifically, with reference now to FIG. 7 it will be noted that the latter patented dental anchor pin is shown generally at 58 and is formed of a plurality of sections 60, 62 which are interconnected by means of a reduced thickness portion 64. The dental anchoring pin can be self-threaded into the bore 50 passing through the passageway 30 defined by the loop 18 at the end of the retaining splint 10. The anchoring pin can be screwed in by means of various tools described in the aforementioned patent.

Additionally, a nut 66 can be threaded onto the section 62 of the anchoring pin 58, and utilized when tightened against the loops to hold the anchoring pin in place. As shown in FIG. 8, the section 62 of the anchoring pin has been inserted into the bore 50 to secure the splint 10 in place. The frangible section 64 has been fractured so that the section 62 remains with the channel 42. By adjusting the height of the threaded nut 66 along the threaded shaft of the section 62 prior to threading the anchoring pin, the depth of insertion of the anchoring pin 62 in the bore 50 can be controlled so as to prevent bottoming out of the bore. Also, the extent to which the pin sticks up from the splint can also be controlled by adjusting the threaded nut 66.

Instead of the nut 66, other types of retainers can be used, such as a snap-on retainer. FIG. 16 shows a rectangular snap-on retainer 66A, and FIG. 17 shows a circular snap-on retainer 66B, each of these retainers having a central opening 65A, 65B therein with a pair of tangs 67A, 67B projecting into the opening to capture the threaded section of the anchoring pin 58 when the pin is inserted therethrough. The retainers 66A, 66B can be disposed along the threaded section in any selected position, either engaging or not engaging the loops of the splint.

It will again be appreciated that a similar arrangement can be placed at the other end of the splint so as to retain both ends in place within the channel. Subsequently, inlay material will be added to fill in the channel and cover the splint.

The splint shown in FIGS. 1 and 2 is actually formed of a single continuous strand of wire suitably bent into shape to provide the wire core, the end loops, as well as the wire coil around the core. For example, the wire can commence at one end of the core shown as 68 in FIG. 1, and extend longitudinally to form one of the strands of wire of the core. The wire can then continue in a looped arrangement to form the concentric end loop 18. The wire can then continue back longitudinally as the other strand of the core until it reaches the opposite end where it will be looped around to form the loop 16. The wire can then be tightly coiled around the two strands of the core with the turns in a juxtaposition until it reaches the opposite end where it terminates at the end 70.

It should be appreciated, that the length of the flexible dental retaining splint can be varied so that splints of different sizes can be provided. Also, in addition to the single core section shown in FIG. 1, a flexible dental retaining splint can be formed having a plurality of sections with the loops at the end of each section being interconnected to the next adjacent section.

Specifically, with reference to FIGS. 9-11, there is shown another embodiment of a flexible dental retaining splint 72. Only a portion of the splint 72 is shown, it being understood that the length could continue at both ends indefinitely. The core section is formed of two wire strands 74, 76 on which are wound the coil 78 with its turns in a juxtaposition. The loops 80 interconnect adjacent sections of the splint and are formed of three independent turns of wire 82, 84, 86. An additional turn of wire 88 passes around the loops to interconnect the coil of one section with the coil of the next adjacent section.

In the manufacture of the splint described in FIGS. 9-11, two wires can be used to form the splint. One of the two wires forms one of the strands of the core of each section and continues to form at least some of the turns in the interconnecting loops. The other of the two wires is utilized to form another one of the strands of the core and also forms some of the turns in the loops.

Alternately, three wires can be utilized with one of the wires acting as the coils about each core and serving as the turn of wire 88 looping from one section to another section. It should be appreciated that other arrangements could be utilized in order to achieve the structure described.

A further embodiment is shown in FIGS. 12-14 where the splint is shown generally at 90 and includes sections of cores including three strands of wire 92, 94, 96 arranged in a triangular fashion. The sections of core have wound about them a wire coil 98 with its turns in a juxtaposition. A loop 100 interconnects adjacent sections of the core with the loop including a plurality of turns of wire 102, 104 and 106. The outside turns 108, 110 are also included to interconnect the adjacent sections.

Though the formation of the arrangement shown in FIG. 12-14 is formed by only three wires, a plurality of wires can be used, some of which serving as the core wires, some of which serving as the coil wires and other of which serving as the loops. Certain of the wires can be utilized for both the loops and the core, others can be utilized for both the coil and the core, while still others may serve as the coil and the loops. The specific procedure for forming the structure can be varied in order to provide the most efficient method and one that will be most convenient for manufacture and subsequent use.

By utilizing the additional strands of wire for the core, a stronger splint is obtained. It should be appreciated that the specific length of each section can be varied in accordance with the ultimate desired length. However, by making short sections with interconnecting loops, it is possible to cut the splint at any desired length and still retain the benefit of flexibility. It should be noted that the loops are available for securing the splint and for maintaining the rigidity of the splint once put in place.

As shown in FIG. 15, a longer channel 110 has been formed in the occlusal surfaces 112, 114, 116 of three adjacent teeth 118, 120, 122. The channel is of an irregular shape and would normally be difficult for a dentist to form a suitably shaped splint. However, by using the arrangement of the embodiment shown in FIGS. 9-14, it is possible to first cut the splint to the desired length as is needed and then shape the cut splint 124 so that it will fit into the irregular shaped channel 110 as shown in FIG. 15. If required, the splint 124 can then be pinned using any of the aforedescribed means. Alternately, or in addition, the splint could be impregnated and/or coated as set forth above. Ultimately, inlay material is placed in the channel 110 to cover the splint 124 and fill the channel.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A flexible dental retaining splint disposable in a channel extending between adjacent teeth, said splint comprising body means for permitting said splint to be bent along its longitudinal length into a selected configuration, said body means including a wire core and a wire coil wound about said core, and wire loops being provided at opposite ends of said wire core, each of said wire loops defining a passageway through said splint, the passageways of said loops facing in the same direction, whereby said loops function to secure said splint in the channel when securing means pass through said passageways.

2. A flexible dental retaining splint as in claim 1, wherein each of said loops comprise a plurality of turns of wire.

3. A flexible dental retaining splint as in claim 2, wherein said core comprises a plurality of strands of wire.

4. A flexible dental retaining splint as in claim 1, wherein said splint comprises a plurality of sections of wound cores with said wire loops interconnecting adjacent sections of said wound cores.

5. A flexible dental retaining splint as in claim 4, wherein at least some strands of wire in said wire core of each section and at least some turns of wire in each interconnecting loop are provided by a continuous wire, and said wire coil for all sections and other turns of wire in each interconnecting loop are provided by another continuous wire.

6. A flexible dental retaining splint as in claim 1, wherein said wire core, said wire loops and said wire coil are provided by a single continuous wire.

7. A flexible dental retaining splint as in claim 1, wherein said wire core and coil include means capable of being hardened to fix the splint in said selected configuration.

8. A flexible dental retaining splint as in claim 7, wherein said hardening means is a heat responsive material.

9. A flexible dental retaining splint as in claim 1, and further including pin means for passing through said passageways and being receivable in bores provided in the teeth for thereby securing said splint within the channel.

10. A flexible dental retaining splint as in claim 9, wherein said pin means includes a dental anchoring pin having an externally threaded shaft and a retainer member disposed on said shaft.

11. A flexible dental retaining splint disposable in a channel extending between adjacent teeth, said splint comprising a core member including at least two adjacent longitudinally extending wire portions, and means disposed around said core member for permitting said splint to be bent by a sufficient force along its longitudinal length into a selected configuration and for maintaining said splint in said selected configuration, said means including a wire coil wound about said core member with turns of said wire coil being in a juxtaposition to provide said splint with substantial rigidity to maintain its configuration when said sufficient force is not applied thereto.

12. A flexible dental retaining splint as in claim 11, wherein wire loops are disposed at opposite ends of said core member to define passageways through said splint, whereby said loops function to secure said splint in the channel when securing means pass through said passageways.

13. A flexible dental retaining splint as in claim 12, wherein said core member, said wire loops and said wire coil consist of a single continuous wire.

14. A flexible dental retaining splint as in claim 12, and further including pin means for passing through said passageways and being receivable in bores provided in the teeth for thereby securing said splint within the channel.

15. A flexible dental retaining splint as in claim 11, wherein said core member and said wire coil include means capable of being hardened to fix said splint in said selected configuration.

* * * * *